US00PP36136P2

(12) United States Plant Patent
Verpaalen

(10) Patent No.: US PP36,136 P2
(45) Date of Patent: Sep. 24, 2024

(54) ***CORNUS* PLANT NAMED 'VERPAALEN3'**

(50) Latin Name: *Cornus alba*
Varietal Denomination: VERPAALEN3

(71) Applicant: Henricus Cornelis E. M. Verpaalen, Zundert (NL)

(72) Inventor: Henricus Cornelis E. M. Verpaalen, Zundert (NL)

( * ) Notice: Subject to any disclaimer, the term of this patent is extended or adjusted under 35 U.S.C. 154(b) by 0 days.

(21) Appl. No.: 18/408,824

(22) Filed: Jan. 10, 2024

(51) Int. Cl.
*A01H 6/00* (2018.01)
*A01H 5/02* (2018.01)

(52) U.S. Cl.
USPC ..... Plt./220

(58) Field of Classification Search
USPC ..... Plt./220
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Cornus* plant named 'VERPAALEN3' is disclosed, characterized by medium green leaves with darker green margins in spring, and dark purple in autumn. Plants are upright and broad. The new cultivar is a *Cornus*, normally used for outdoor ornamental purposes.

3 Drawing Sheets

Latin name of the genus and species: *Cornus alba.*
Cultivar denomination: 'VERPAALEN3'.

BACKGROUND OF THE INVENTION

The new *Cornus* cultivar is a product of a planned breeding program conducted by the inventor. The new cultivar is the result of a naturally occurring mutation of *Cornus alba* 'Miracle', unpatented. *Cornus* 'VERPAALEN3' was found and selected by the inventor in a field at a nursery in Zundert, The Netherlands, in April 2020.

Asexual reproduction of the new cultivar was performed by vegetative cuttings. This was first performed at the same nursery in Zundert, The Netherlands, in April 2020, and has shown that the unique features of this cultivar are stable and reproduced true to type in multiple successive generations.

SUMMARY OF THE INVENTION

The cultivar 'VERPAALEN3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VERPAALEN3' These characteristics in combination distinguish 'VERPAALEN3' as a new and distinct *Cornus* cultivar:

1. Leaves are medium green with darker green margins in spring; dark green in summer; dark purple in autumn.
2. Red stems in autumn/winter.

PARENT COMPARISON

Plants of the new cultivar *Cornus* 'VERPAALEN3' are similar to plants of *Cornus* 'Miracle' in most horticultural characteristics; however, plants of the new cultivar 'VERPAALEN3' differ in the following:

1. Foliage color of the new cultivar is medium green with darker green margins in spring; dark green in summer; dark purple in autumn. Foliage color of the parent cultivar is green and white with a pink border in spring and early summer; purple-pink from summer to autumn.

COMMERCIAL COMPARISONS

Plants of the new cultivar 'VERPAALEN3' are comparable to the commercial variety *Cornus* 'Elegantissima', unpatented. The two *Cornus* varieties are similar in most horticultural characteristics, however, the new cultivar 'VERPAALEN3' differs in the following:

1. Foliage color of the new cultivar is medium green with darker green margins in spring; dark green in summer; dark purple in autumn. Foliage color of this comparator is green with white margins, occasionally light pink.

Plants of the new cultivar 'VERPAALEN3' are comparable to the commercial cultivar *Cornus* 'Cream Cracker', U.S. Plant Pat. No. 12,830. The two *Cornus* varieties are similar in most horticultural characteristics; however, the new cultivar 'VERPAALEN3' differs in the following:

1. Foliage color of the new cultivar is medium green with darker green margins in spring; dark green in summer; dark purple in autumn. Foliage color of this comparator is green with white margins.

BRIEF DESCRIPTION OF THE PHOTOGRAPHS

The accompanying photographs illustrate in full color various distinguishing characteristic of the new cultivar, 'VERPAALEN3' grown outdoors in Zundert, the Netherlands. The photographs were taken using conventional techniques and although colors may appear different from actual colors due to light reflectance it is as accurate as possible by conventional photographic techniques.

DETAILED BOTANICAL DESCRIPTION

Figure 1:
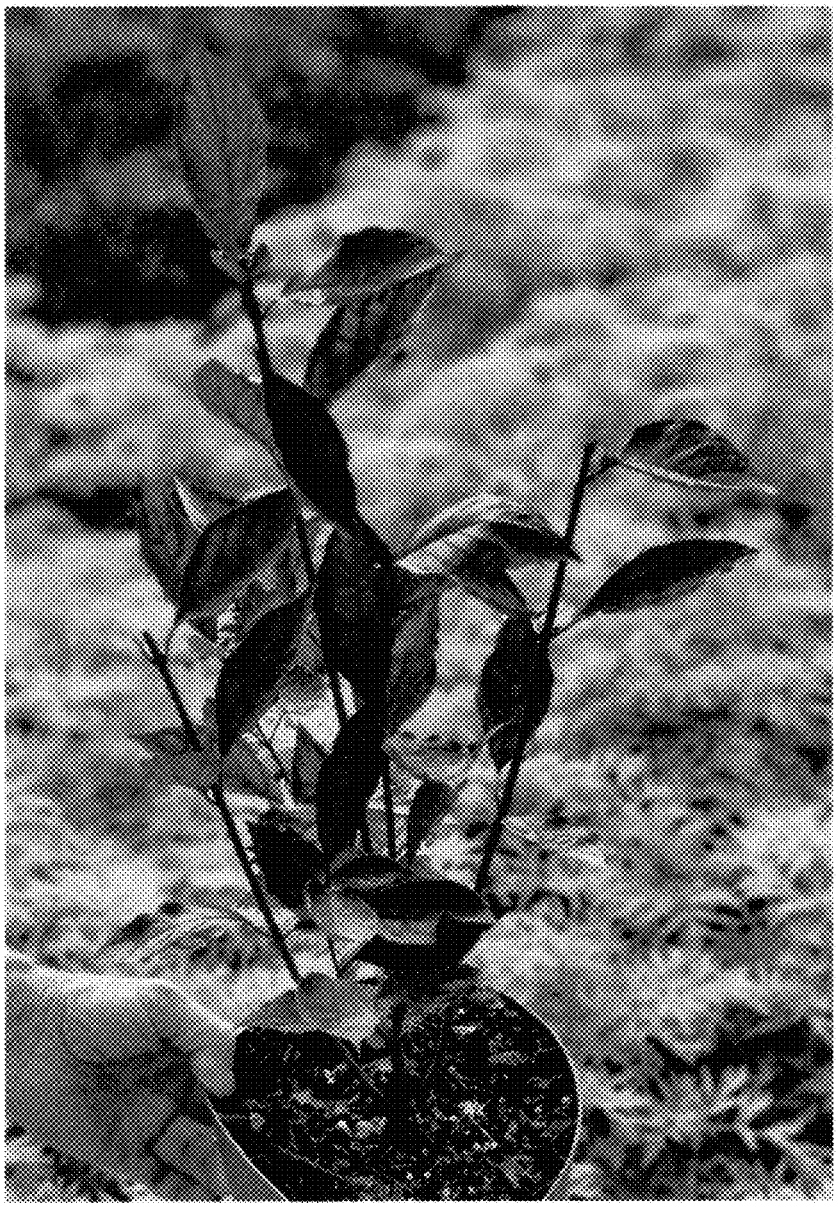
FIG. 1 illustrates a potted plant of approximately 9 months in a 3 liter pot.
Figure 2:
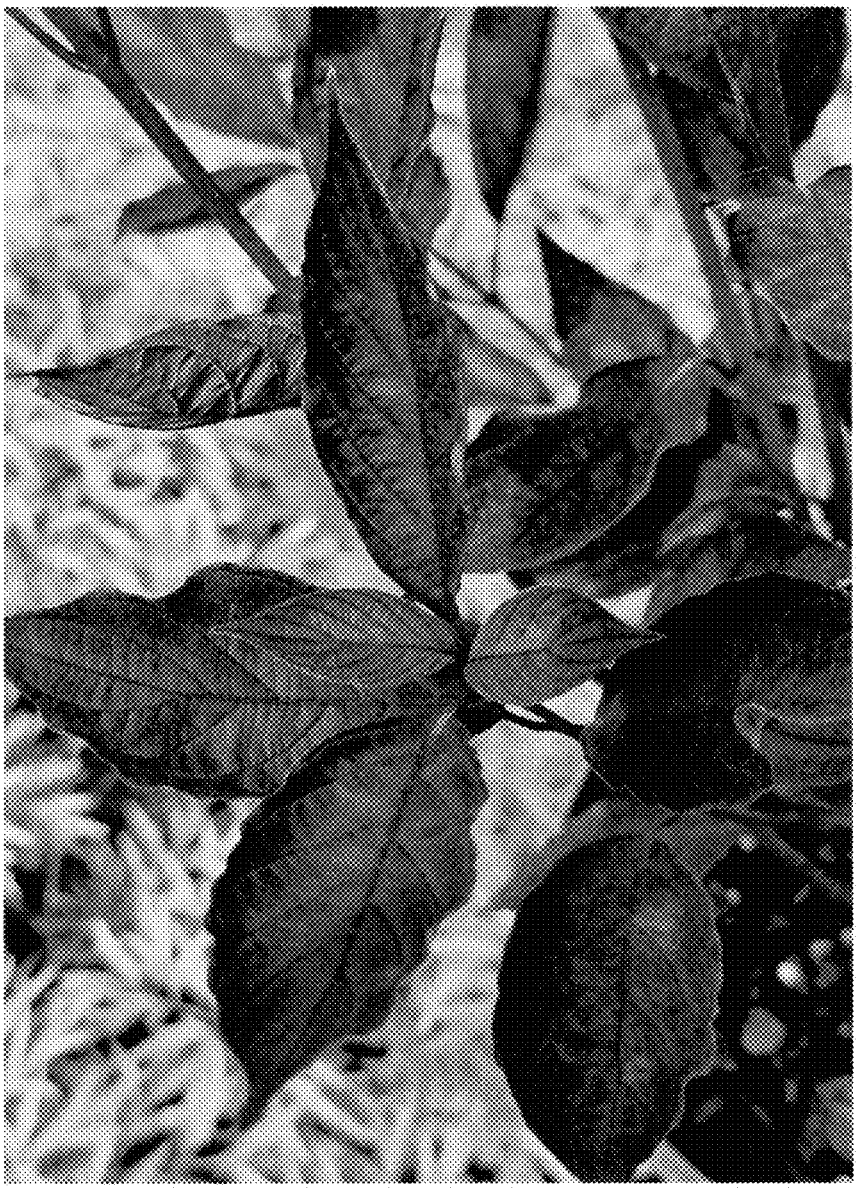
FIG. 2 illustrates a close-up view of the foliage.
Figure 3:
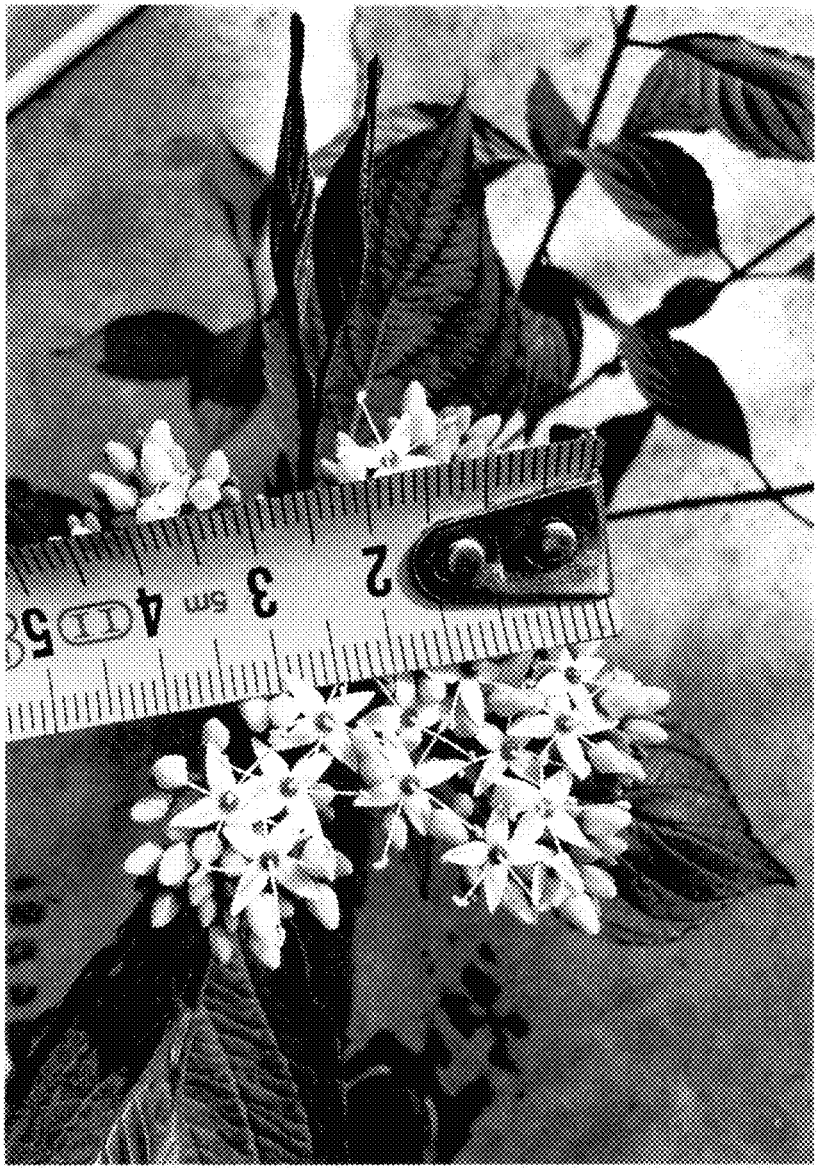
FIG. 3 illustrates a typical inflorescence and foliage in late Spring.

In the following description, color references are made to The Royal Horticultural Society Colour Chart 6th Edition 2015 except where general terms of ordinary dictionary significance are used. The following observations and measurements describe 'VERPAALEN3' plants grown outdoors in Zundert, the Netherlands. The growing temperature ranged from approximately 8° C. to 32° C. during the day and from approximately 1° C. to 12° C. during the night. General light conditions are normal sunlight and numerical values represent averages of typical plant types.

Botanical classification: *Cornus alba* 'VERPAALEN3'.

Propagation:

*Type of propagation typically used.*—Terminal vegetative cuttings.

*Time to initiate roots.*—4 weeks.

*Time to produce a rooted cutting.*—4 months to a 9 cm pot.

*Root description.*—Very thin, fibrous, not fleshy, freely branching. New roots colored near R.H.S. Yellow-White 158D. Older roots colored near Grey-Brown 199D.

Plant:

*Age of plant described.*—1.5 years old from a rooted cutting.

*Container size.*—19 cm pot.

*Plant type.*—Deciduous shrub.

*Growth habit.*—Upright, broad.

*Plant spread.*—50 cm in a pot; 2 m as a mature plant in a field.

*Plant height.*—90 cm in a pot; 2 m as a mature plant in a field.

*Growth rate.*—Moderate to vigorous.

*Stem.*—Main basal branches: Quantity: 1 basal stem, 3 lateral branches. Length: 6 cm. Diameter: 1.2 cm. Lateral branches: Quantity: 3 per basal stem. Length: 37 cm. Diameter: 7 mm. Color: New growth: R.H.S. Purple-Brown 183A and 187B on top. Old growth: R.H.S. Purple-Brown 166A. Shape: Oval. Pubescence: Very sparsely covered with short, pale grey hairs. Other: Stems have light brown lenticels less than 1 mm in length.

*Internode length.*—11 cm.

Foliage:

*Leaf.*—Arrangement: Opposite. Division: Simple. Length: 10.5 cm. Width: 5.7 cm. Shape: Elliptic. Apex: Acuminate. Base: Cuneate. Margin: Entire. Texture of top surface: Slightly pubescent. Color: Young foliage upper side: R.H.S. Brown 200A. Young foliage, under side: R.H.S. Grey-Green 191A with Brown N220B towards margins (faded). Mature foliage upper side: R.H.S. Brown 200A with NN137A. Mature foliage under side: R.H.S. Grey-Green 191A with Brown N220B towards margins (faded). Venation: Type: Pinnate. Color, upper side: R.H.S. Purple-Brown 187B. Color, under side: R.H.S. Yellow-Green 145B to 145C. Purple-Brown 183A towards base. Petiole: Length: Up to 2 cm. Diameter: 2 mm. Color: Upper side: R.H.S. Purple-Brown 187A. Under side: R.H.S. Purple-Brown 183A.

Flower:

*Natural flowering season.*—Late spring to early summer.

*Arrangement.*—Compound corymb.

*Quantity per lateral stem.*—23 open flowers; about 150 flowers and buds.

*Quantity per plant.*—1 inflorescence.

*Inflorescence size.*—Width: About 5 cm. Length: About 2.3 cm.

*Individual flowers.*—Type: Single. Diameter: About 1 cm. Depth: About 4 mm. Persistence: Self-cleaning. Fragrance: None.

*Petals.*—Arrangement: Cross. Number: 4. Shape: Ovate. Margin: Entire. Apex: Acute. Base: Truncate. Length: About 4 mm. Width: 2 mm. Texture: Smooth. Color: When opening: R.H.S. White N155A. Fully opened: R.H.S. White N155A.

*Bud.*—Shape: Ovoid. Length: 3 to 4 mm. Diameter: About 3 mm. Color: Young buds: R.H.S. Yellow-Green 145C. Older buds: R.H.S. White N155A.

*Calyx.*—Shape: Campanulate. Length: About 2 mm. Diameter: About 2 mm.

*Sepals.*—Arrangement: Fused to calyx. Margin: Entire.

*Peduncle.*—Length: 2.8 cm; secondary peduncle 0.6 cm. Diameter: 2 mm; secondary peduncle 1 mm. Texture: Slightly pubescent. Color: R.H.S. Green 146C, with hints of Purple-Brown 183A. Strength: Strong.

*Pedicel.*—Length: About 0.8 cm. Diameter: Less than 1 mm. Texture: Slightly pubescent. Color: R.H.S. Green 146C, with hints of Purple-Brown 183A.

Reproductive organs:

*Stamens.*—Number: 4. Color: R.H.S. White N155A. Length: 5 mm.

*Anthers.*—Shape: Oblong. Length: 1 mm. Color: R.H.S. White 158D. Pollen: Few.

*Pistil.*—Number: 1. Length: 1.5 mm.

*Stigma.*—Shape: Globular. Color: R.H.S. Purple-Red 185B.

Other characteristics:

*Fruits and seeds.*—Not observed to date.

*Disease/pest resistance.*—Neither resistance nor susceptibility to other normal diseases and pests of *Cornus* observed.

*Temperature range.*—Cold hardy to −30° C.

What is claimed is:

1. A new and distinct cultivar of *Cornus* plant named 'VERPAALEN3' as herein illustrated and described.

* * * * *